United States Patent

Fuchs et al.

[11] Patent Number: 5,840,981
[45] Date of Patent: Nov. 24, 1998

[54] PROCESS FOR PRODUCING N-METHYL-2(3, 4 DIMETHOXYPHENYL)-ETHYLAMINE

[75] Inventors: Eberhard Fuchs, Frankenthal; Horst Zimmermann, Mannheim; Tom Witzel, Ludwigshafen; Boris Breitscheidel, Fulda; Rainer Becker, Bad Dürkheim; Horst Nauhauser, Dudenhofen, all of Germany

[73] Assignee: BASF Aktiengesellschaft, Ludwigshafen, Germany

[21] Appl. No.: 945,530

[22] PCT Filed: May 4, 1996

[86] PCT No.: PCT/EP96/01861

§ 371 Date: Jan. 23, 1998

§ 102(e) Date: Jan. 23, 1998

[87] PCT Pub. No.: WO96/36589

PCT Pub. Date: Nov. 21, 1996

[30] Foreign Application Priority Data

May 17, 1995 [DE] Germany ............. 195 18 018.6
May 17, 1995 [DE] Germany ............. 195 18 038.0
Feb. 23, 1996 [DE] Germany ............. 196 06 729.4

[51] Int. Cl.$^6$ ................................. C07C 209/22
[52] U.S. Cl. .................... 564/395; 564/399; 564/415
[58] Field of Search ..................... 564/415, 395, 564/399

[56] References Cited

FOREIGN PATENT DOCUMENTS 389 876  10/1990  European Pat. Off. .
33 38 681  10/1983  Germany .

OTHER PUBLICATIONS

Sogo Rikogaku Kenkyuka Hokoku (Kyushu Daigaku Daigakuin), 16(3) 307–10 (1994).
*Archiv. Der Pharmazie*, vol. 271, 1993, pp. 439–445, Kindler et al.

*Primary Examiner*—Brian M. Burn
*Attorney, Agent, or Firm*—Keil & Weinkauf

[57] ABSTRACT

A process for preparing N-methyl-2-(3,4-dimethoxyphenyl) -ethylamine comprises hydrogenating 3,4-dimethoxyphenylacetonitrile with a methylamine of the general formula I

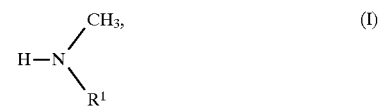

where $R^1$ is hydrogen, benzyl or tert-butyl, and hydrogen in the presence of a supported catalyst which comprises from 0.05 to 50% by weight of copper chromite, copper, silver, gold, iron, cobalt, nickel, ruthenium, rhodium, palladium, osmium, iridium, platinum or mixtures thereof, in the presence or absence of water at from 20° to 200° C. under from 1 to 300 bar.

10 Claims, No Drawings

PROCESS FOR PRODUCING N-METHYL-2(3, 4 DIMETHOXYPHENYL)-ETHYLAMINE

The present invention relates to a process for preparing N-methyl-2-(3,4-dimethoxyphenyl)ethylamine (N-methylhomoveratrylamine) by reacting 3,4-dimethoxyphenylacetonitrile (veratryl cyanide) with a methylamine or substituted methylamine, where the substituent is a group which can be eliminated under the reaction conditions, and hydrogen in the presence of a supported catalyst which comprises copper chromite, an element of group IB or VIII of the Periodic Table of the Elements or mixtures thereof, in the presence or absence of water at elevated temperatures.

DE-A-33 38 681 discloses the catalytic hydrogenation of veratryl cyanide with a ten-fold molar excess of methylamine on a nickel catalyst. Homoveratrylamine is obtained as byproduct with more than 3% selectivity and has to be removed by adding benzaldehyde.

Arch. Pharm., 271 (1933) 431–448 discloses the hydrogenation of veratryl cyanide to N-methylhomoveratrylamine in the presence of methylamine and palladium black as catalyst. However, the yield is unsatisfactory in terms of the palladium employed.

Ind. Eng. Chem. Prod. Res. Dev., 6 (1967) 142–144 discloses the catalytic hydrogenation of nitriles to primary, secondary and tertiary amines on palladium and platinum catalysts, primarily leading to tertiary amines. Methanol is described as catalyst poison therein. Rhodium is said to be suitable for preparing secondary amines.

By contrast, the hydrogenation of valeronitrile with butylamine on palladium and platinum leads to butylpentylamine, but the conversions are low at 54% and 23% respectively.

Catalysis of Organic Reactions, (1992), 93–104 advises against the use of acidic catalysts such as titanium oxide or alumina, and the use of polar solvents in general and of methanol in particular, in the preparation of secondary amines from nitrites and primary amines.

It is an object of the present invention to remedy the abovementioned disadvantages.

We have found that this object is achieved by a novel and improved process for preparing N-methyl-2-(3,4-dimethoxyphenyl)ethylamine, which comprises hydrogenating 3,4-dimethoxyphenylacetonitrile with a methylamine of the general formula I

where $R^1$ is hydrogen, benzyl or tert-butyl, and hydrogen in the presence of a catalyst which comprises from 0.05 to 50% by weight of copper chromite, copper, silver, gold, iron, cobalt, nickel, ruthenium, rhodium, palladium, osmium, iridium, platinum or mixtures thereof, in the presence or absence of water at from 50° to 200° C. under from 1 to 300 bar.

The process according to the invention can be carried out in the following way:

3,4-dimethoxyphenylacetonitrile with a methylamine I and hydrogen can be reacted with from 0 to 30, preferably 0.05 to 2.5, particularly preferably 0.1 to 2%, by weight of water in the presence of a supported catalyst which comprises copper chromite, an element of group IB or VIII of the Periodic Table of the Elements or mixtures thereof, batchwise or continuously, preferably in a pressure vessel or reactor, such as an autoclave or tubular reactor, particularly preferably continuously in a tubular reactor, at from 20° to 200° C., preferably 50° to 180° C., particularly preferably 70° to 160° C., under from 1 to 300 bar, preferably 30 to 300 bar, particularly preferably 50 to 270 bar, with or without addition of a solvent. Working up can take place by conventional methods, for example by distillation.

Suitable methylamines I are in particular methylamine itself and those substituted methylamines I whose substituent is a group which can be eliminated under the reaction conditions, such as benzyl and tert-butyl, ie. benzylmethylamine and tert-butylmethylamine, preferably benzylmethylamine.

The benzyl or tert-butyl group can preferably be eliminated under the hydrogenation conditions, thermally or in the presence of inorganic or organic acids, such as sulfuric acid, hydrochloric acid, methylsulfonic acid or acetic acid, or acidic catalysts such as ion exchangers or zeolites.

The molar ratio of methylamine to 3,4-dimethoxyphenylacetonitrile is, as a rule, from 1:1 to 15:1, preferably 1.5:1 to 10:1, particularly preferably 2:1 to 5:1.

Suitable solvents are alcohols having 1 to 8 carbon atoms, preferably alcohols having 1 to 4 carbon atoms, N-substituted pyrrolidones such as N-methylpyrrolidone, ethers such as tetrahydrofuran, aromatic hydrocarbons such as benzene, toluene or the xylenes, or the methylamine itself. Methanol, N-methylpyrrolidone, tetrahydrofuran, methylbenzylamine and methylamine are particularly preferred.

Suitable supported catalysts comprising copper chromite, an element of group IB or VIII of the Periodic Table of the Elements or mixtures thereof are those which have a total content of copper chromite, copper, silver, gold, iron, cobalt, nickel, ruthenium, rhodium, palladium, osmium, iridium, platinum or mixtures thereof, preferably copper chromite, copper, palladium, platinum or mixtures thereof, particularly preferably palladium, platinum or mixtures thereof, especially platinum, of, as a rule, from 0.05 to 50% by weight, preferably 0.1 to 10% by weight, particularly preferably 0.5 to 2% by weight, on a carrier, but preferably consist thereof.

Examples of suitable carriers are active carbons, silicon carbide or oxides such as alumina, silica, titanium dioxide, zirconium dioxide, zinc oxide, magnesium oxide or mixtures thereof, which may be doped with alkali metal and/or alkaline earth metal oxides, preferably γ-alumina, silica or alumina/silica mixtures. The carriers can be used, for example, as extrudates, pellets or tablets.

The catalysts according to the invention are generally prepared by industrially known processes, and can preferably be prepared by the pore impregnation process. This can entail the metal precursor being dissolved in an amount of water corresponding to the pore volume of the carrier, impregnating the carrier with the solution, and subsequently drying the catalyst at, for example, from 80° to 170° C., preferably 100° to 150° C., for, example, from 1 to 48 h, preferably 12 to 24 h. The drying can be carried out with or without agitation. A possible alternative to pore impregnation is impregnation with an amount of solvent which is larger than the pore volume of the carrier (impregnation with supernatant solution). The dried catalyst can then be calcined, as a rule in a stream of air, for example at from 300° to 700° C., preferably 400° to 600° C., for from 0.5 to 10 h, preferably 1 to 3 h.

Suitable metal precursors are metal salts such as nitrates, nitrosyl nitrates, halides, carbonates, carboxylates, acetylacetonates, chloro complexes, nitrito complexes or amine complexes, preferably nitrates, chlorides or chloro complexes.

In the case of catalysts which contain a plurality of metals as active components, the metal precursors can be impregnated simultaneously or successively. In the case of separate impregnation, the catalyst is dried after each impregnation step at from 80° to 170° C., preferably 100° to 150° C., for from 1 to 48 h, preferably 12 to 24 h. The sequence of impregnation with the active components can be chosen as desired.

N-Methyl-2-(3,4-dimethoxyphenyl)ethylamine [N-methylhomoveratrylamine] is an intermediate in the synthesis of the drug verapamil (U.S. Pat. No. 3,261,859).

EXAMPLES

Example 1

205 ml of a 28% strength solution of veratryl cyanide in methylbenzylamine (molar ratio 1:3.7) were pumped each hour upwards through a vertical hydrogenation reactor (diameter: 16 mm; height of packing: 600 mm; oil-heated jacket) which was packed with 511 g (800 ml) of catalyst (0.5% by weight of palladium on alumina) at 160° C. under 200 bar. Simultaneously, 100 l(STP)/h hydrogen were passed upwards through the reactor. After decompression to atmospheric pressure, excess methylbenzylamine was removed by distillation, and the discharge was analyzed by quantitative gas chromatography. 40 g (70%) of N-methylhomoveratrylamine were obtained per hour.

Example 2

7 g (40 mmol) of veratryl cyanide and 25 g (200 mmol) of methylbenzylamine were heated together with 3 g of a catalyst containing 4% by weight palladium on alumina in a 300 ml autoclave to 100° C. and were hydrogenated with hydrogen under 200 bar for 10 h. Decompression resulted in 6.2 g (81%) of N-methylhomoveratrylamine with 100% conversion.

Example 3

400 ml of a 37% strength solution of veratryl cyanide in N-methylpyrrolidone with 3% by weight of water and 280 ml of liquid methylamine (molar ratio 1:10) were pumped each hour upwards through a vertical hydrogenation reactor (diameter: 27 mm; height of packing: 1500 mm; oil-heated jacket) which was packed with 800 ml of a catalyst consisting of 0.5% by weight of palladium on γ-alumina as 4 mm pellets at 140° C. under 200 bar. Simultaneously, 200 l(STP)/h hydrogen were passed upwards through the reactor. After decompression to atmospheric pressure, excess methylamine was removed by distillation, and the discharge was analyzed by quantitative gas chromatography.

Over a running time of more than 1000 hours, N-methyl-2-(3,4-dimethoxyphenyl)ethylamine (N-methylhomoveratrylamine) was obtained in a yield of 90%, with quantitative conversion of 3,4-dimethoxyphenylacetonitrile (veratryl cyanide). The homoveratrylamine content was below 1%.

Preparation of the catalyst

Catalyst A: 0.5% by weight palladium on $Al_2O_3$ 1000 g of an alumina carrier in the form of 2 to 4 mm pellets with an apparent density of 755 g/l, a pore volume of 0.57 $cm_3$/g and a surface area of 238 $m^2$/g were impregnated with 570 ml of a solution of palladium(II) nitrate in nitric acid and dried without agitation at 120° C. for 18 h and calcined at 450° C. for 3 h.

Catalyst B: 1% by weight platinum on $Al_2O_3$ 1613 g of an alumina carrier in the form of 4 mm extrudates with an apparent density of 560 g/l, a pore volume of 0.68 $cm^3$/g and a surface area of 203 $m^2$/g were impregnated with 1097 ml of an aqueous platinum(II) nitrate solution and dried without agitation at 120° C. for 20 h and calcined at 450° C. for 3 h.

Catalyst C: 0.8% by weight platinum on $SiO_2/Al_2O_3$ 1032 g of a silica/alumina carrier consisting of 80% by weight silica and 20% by weight alumina, in the form of 3 mm extrudates with an apparent density of 463 g/l, a pore volume of 0.94 $cm^3$/g and a surface area of 167 $m^2$/g were impregnated with 970 ml of a solution of platinum(II) chloride in hydrochloric acid and dried without agitation at 120° C. for 20 h and calcined at 450° C. for 3 h.

Catalyst D: 0.4% by weight Pd/0.4% by weight Pt on $SiO_2/Al_2O_3$

The silica/alumina carrier described for catalyst C was impregnated with 970 ml of a solution containing palladium (II) chloride and platinum(II) chloride in hydrochloric acid and dried without agitation at 120° C. for 20 h and calcined at 450° C. for 3 h.

Catalyst E: 0.8% by weight palladium on $SiO_2/Al_2O_3$

The silica/alumina carrier described for catalyst C was impregnated with 970 ml of a solution containing palladium (II) chloride in hydrochloric acid and dried without agitation at 120° C. for 20 h and calcined at 450° C. for 3 h.

Catalyst F: 0.8% by weight palladium on $SiO_2/Al_2O_3$

Preparation took place as for catalyst E but the impregnated catalyst was dried with agitation in a rotating tube at 120° C. for 1 h and calcined at 450° C. for 1 h.

Catalyst G: 0.8% by weight palladium on $SiO_2$ 1520 g of a silica carrier in the form of 3 to 5 mm pellets with an apparent density of 489 g/l, a pore volume of 0.92 $cm^3$/g and a surface area of 336 $m^2$/g were impregnated with 1398 ml of a solution of palladium(II) chloride in hydrochloric acid and dried with agitation in a rotating tube at 120° C. for 1 h and calcined at 450° C. for 1 h.

Examples 4 to 11

27 ml of a 37% strength veratryl cyanide solution and 10 ml of liquid methylamine (molar ratio 1:5) were pumped each hour upwards through a vertical hydrogenation reactor (diameter: 16 mm; height of packing: 400 mm; oil-heated jacket) which was packed with 80 ml of a catalyst from the following table at 140° C. under 80 bar. Simultaneously, 10 l(STP)/h hydrogen were passed upwards through the reactor. After decompression to atmospheric pressure, excess methylamine was removed by distillation, and the discharge was analyzed by quantitative gas chromatography.

The results are compiled in the following table.

TABLE

| Example No. | Catalyst | Solvent | Conversion [%] | Selectivity [%] | Yield [%] | HVA [%] |
|---|---|---|---|---|---|---|
| 4 | A | Methanol | 95 | 65 | 60 | <1 |
| 5 | B | Methanol | 100 | 85 | 83 | <1 |
| 6 | C | Methanol | 99 | 94 | 91 | <1 |
| 7 | D | Methanol | 100 | 75 | 73 | <1 |
| 8 | E | Methanol | 100 | 80 | 78 | <1 |
| 9 | E | NMP | 99 | 95 | 88 | <1 |
| 10 | F | NMP | 99 | 93 | 84 | <1 |
| 11 | G | NMP | 99 | 99 | 94 | <1 |

Conversion = veratryl cyanide conversion
Selectivity = N-Methylhomoveratrylamine selectivity
NMP = N-Methylpyrrolidone
HVA = Homoveratrylamine

We claim:
1. A process for preparing N-methyl-2-(3,4-dimethoxyphenyl)ethylamine, which comprises hydrogenat- ing 3,4-dimethoxyphenylacetonitrile with a methylamine of the general formula

where $R^1$ is hydrogen, benzyl or tert-butyl, and hydrogen in the presence of a catalyst which comprises from 0.05 to 50% by weight of copper chromite, copper, silver, gold, iron, cobalt, nickel, ruthenium, rhodium, palladium, osmium, iridium, platinum or mixtures thereof, in the presence or absence of water at from 20° to 200° C. under from 1 to 300 bar.

2. A process for preparing N-methyl-2-(3,4-dimethoxyphenyl)ethylamine as claimed in claim 1, wherein the compound of the general formula I where $R^1$ is hydrogen or benzyl is used as methylamine.

3. A process for preparing N-methyl-2-(3,4-dimethoxyphenyl)ethylamine as claimed in claim 1, wherein the compound of the general formula I where $R^1$ is hydrogen is used as methylamine.

4. A process for preparing N-methyl-2-(3,4-dimethoxyphenyl)ethylamine as claimed in claim 1, wherein the supported catalyst comprises from 0.1 to 10% by weight of copper chromite, copper, silver, gold, iron, cobalt, nickel, ruthenium, rhodium, palladium, osmium, iridium, platinum or mixtures thereof.

5. A process for preparing N-methyl-2-(3,4-dimethoxyphenyl)ethylamine as claimed in claim 1, wherein the supported catalyst comprises copper chromite, copper, nickel, ruthenium, palladium, platinum or mixtures thereof.

6. A process for preparing N-methyl-2-(3,4-dimethoxyphenyl)ethylamine as claimed in claim 1, wherein the supported catalyst comprises ruthenium, palladium, platinum or mixtures thereof.

7. A process for preparing N-methyl-2-(3,4-dimethoxyphenyl)ethylamine as claimed in claim 1, wherein the supported catalyst comprises palladium.

8. A process for preparing N-methyl-2-(3,4-dimethoxyphenyl)ethylamine as claimed in claim 1, wherein the molar ratio of water to 3,4-dimethoxyphenylacetonitrile is from 0.05:1 to 2.5:1.

9. A process for preparing N-methyl-2-(3,4-dimethoxyphenyl)ethylamine as claimed in claim 1, wherein the molar ratio of methylamine to 3,4-dimethoxyphenylacetonitrile is from 1:1 to 15:1.

10. A process for preparing N-methyl-2-(3,4-dimethoxyphenyl)ethylamine as claimed in claim 1, wherein active carbon, alumina, silica, titanium dioxide, zirconium dioxide, zinc oxide, magnesium oxide, silicon carbide or mixtures thereof are used as carrier.

* * * * *

UNITED STATES PATENT AND TRADEMARK OFFICE
CERTIFICATE OF CORRECTION

PATENT NO.: 5,840,981

DATED: November 24, 1998

INVENTOR(S): FUCHS et al.

It is certified that error appears in the above-identified patent and that said Letters Patent is hereby corrected as shown below:

Title page, item [54]
In the inventors, the last inventor's last name "Nauhauser" should be --Neuhauser--.

Claims 1 to 10, the second line of each, "dimethoxyphenyl)ethylamine" should be --dimethoxyphenyl)-ethylamine Signed and Sealed this Thirtieth Day of March, 1999

Attest:

Q. TODD DICKINSON

Attesting Officer

Acting Commissioner of Patents and Trademarks